US012806402B2

United States Patent
(12) United States Patent
Schlebusch et al.

(10) Patent No.: US 12,806,402 B2
(45) **Date of Patent: *Nov. 24, 2026**

(54) METHOD FOR DETERMINING A FLOW RATE OF A FLUID FLOWING THROUGH A CARDIAC ASSIST SYSTEM

(71) Applicant: KARDION GMBH, Stuttgart (DE)

(72) Inventors: Thomas Alexander Schlebusch, Renningen (DE); Tobias Schmid, Stuttgart (DE)

(73) Assignee: Kardion GmbH, Stuttgart (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/030,573

(22) Filed: Jan. 17, 2025

(65) Prior Publication Data

US 2025/0235687 A1 Jul. 24, 2025

Related U.S. Application Data

(63) Continuation of application No. 15/734,353, filed as application No. PCT/EP2019/064804 on Jun. 6, 2019, now Pat. No. 12,201,821.

(30) Foreign Application Priority Data

Jun. 6, 2018 (DE) ........................ 102018208929.9

(51) Int. Cl.
*A61M 60/523* (2021.01)
*A61M 60/178* (2021.01)
(Continued)

(52) U.S. Cl.
CPC ........ *A61M 60/178* (2021.01); *A61M 60/216* (2021.01); *A61M 60/523* (2021.01);
(Continued)

(58) Field of Classification Search
CPC ................................ A61B 8/06; A61B 60/523
See application file for complete search history.

(56) References Cited

U.S. PATENT DOCUMENTS 4,680,730 A 7/1987 Omoda
5,606,972 A 3/1997 Routh
(Continued)

FOREIGN PATENT DOCUMENTS

CN 215841206 2/2022
CN 217828630 11/2022
(Continued)

OTHER PUBLICATIONS

Chung et al., "Improved Efficiency Characteristics of Wireless Power Charging System for Superconducting MAGLEV Train Using Inserted Permanent Magnets," 2018 IEEE International Symposium on Electromagnetic Compatibility, 2018, pp. 564-567.
(Continued)

*Primary Examiner* — Colin T. Sakamoto
*Assistant Examiner* — Tommy T Ly
(74) *Attorney, Agent, or Firm* — Knobbe, Martens, Olson & Bear, LLP

(57) ABSTRACT

The invention relates to a method for determining a flow rate of a fluid flowing through an implanted vascular assist system, said method comprising the following steps: a) carrying out a first pulsed Doppler measurement at a first pulse repetition rate by means of an ultrasonic sensor of the assist system; b) carrying out a second pulsed Doppler measurement at a second pulse repetition rate by means of the ultrasonic sensor of the assist system, wherein the second pulse repetition rate differs from the first pulse repetition rate; c) determining the flow rate using measurement results of the first pulsed Doppler measurement and the second pulsed Doppler measurement.

19 Claims, 3 Drawing Sheets

(51) Int. Cl.
*A61M 60/216* (2021.01)
*A61M 60/816* (2021.01)

(52) U.S. Cl.
CPC ... *A61M 60/816* (2021.01); *A61M 2205/3334* (2013.01); *A61M 2210/125* (2013.01)

(56) References Cited

U.S. PATENT DOCUMENTS

| | | | | |
|---|---|---|---|---|
| 5,695,471 | A | 12/1997 | Wampler | |
| 5,865,759 | A | 2/1999 | Koblanski | |
| 6,167,765 | B1 | 1/2001 | Weitzel | |
| 6,293,901 | B1 * | 9/2001 | Prem | A61M 60/894 623/3.28 |
| 7,010,954 | B2 | 3/2006 | Siess | |
| 7,526,338 | B1 | 4/2009 | Gill | |
| 7,527,599 | B2 | 5/2009 | Hickey | |
| 9,427,509 | B2 | 8/2016 | Vodermayer | |
| 9,789,236 | B2 | 10/2017 | Bonde | |
| 10,639,460 | B2 | 5/2020 | Nitzan et al. | |
| 10,653,871 | B2 | 5/2020 | Nitzan et al. | |
| 10,864,308 | B2 | 12/2020 | Muller et al. | |
| 11,724,091 | B2 | 8/2023 | Siess et al. | |
| 12,059,559 | B2 | 8/2024 | Muller et al. | |
| D1,043,730 | S | 9/2024 | Lussier et al. | |
| D1,043,731 | S | 9/2024 | Lussier et al. | |
| 12,076,544 | B2 | 9/2024 | Siess et al. | |
| 12,097,016 | B2 | 9/2024 | Goldvasser | |
| 12,102,815 | B2 | 10/2024 | Dhaliwal et al. | |
| 12,144,650 | B2 | 11/2024 | Spanier et al. | |
| 12,144,976 | B2 | 11/2024 | Baumbach et al. | |
| 12,178,554 | B2 | 12/2024 | Stotz et al. | |
| 12,179,009 | B2 | 12/2024 | El Katerji et al. | |
| 12,183,459 | B2 | 12/2024 | Agnello et al. | |
| 12,194,287 | B2 | 1/2025 | Kassel et al. | |
| 12,201,821 | B2 | 1/2025 | Schlebusch et al. | |
| 12,211,615 | B2 | 1/2025 | Nix et al. | |
| D1,060,379 | S | 2/2025 | Lussier et al. | |
| 12,213,771 | B2 | 2/2025 | Curran et al. | |
| 12,217,850 | B2 | 2/2025 | Agnello | |
| 12,222,267 | B2 | 2/2025 | Stotz et al. | |
| 12,251,551 | B2 | 3/2025 | Liu et al. | |
| 12,257,424 | B2 | 3/2025 | Schlebusch et al. | |
| 12,268,861 | B2 | 4/2025 | D'Ambrosio et al. | |
| 12,296,158 | B2 | 5/2025 | Higgins et al. | |
| 12,296,159 | B2 | 5/2025 | Schilling et al. | |
| 12,310,621 | B2 | 5/2025 | Murphy | |
| 12,310,708 | B2 | 5/2025 | Schlebusch et al. | |
| 12,311,160 | B2 | 5/2025 | Schlebusch et al. | |
| 12,324,906 | B2 | 6/2025 | Baumbach et al. | |
| 12,329,501 | B2 | 6/2025 | Moyer et al. | |
| 12,329,956 | B2 | 6/2025 | Sunagawa | |
| 12,329,959 | B2 | 6/2025 | Hassan et al. | |
| 12,343,518 | B2 | 7/2025 | Tuval et al. | |
| D1,090,610 | S | 8/2025 | Kroeker et al. | |
| 12,377,256 | B2 | 8/2025 | Stotz et al. | |
| 12,390,168 | B2 | 8/2025 | Katerji et al. | |
| 12,397,099 | B2 | 8/2025 | Germain et al. | |
| 12,397,147 | B2 | 8/2025 | Siess et al. | |
| D1,092,492 | S | 9/2025 | Lussier et al. | |
| 12,409,311 | B2 | 9/2025 | Jahangir et al. | |
| 12,409,313 | B2 | 9/2025 | Eggen et al. | |
| 12,424,306 | B2 | 9/2025 | Liu et al. | |
| 12,424,315 | B2 | 9/2025 | Nix et al. | |
| 12,434,060 | B2 | 10/2025 | Tan et al. | |
| 12,440,665 | B2 | 10/2025 | Tuval et al. | |
| 12,445,278 | B2 | 10/2025 | Agnello | |
| 12,451,230 | B2 | 10/2025 | El Katerji et al. | |
| 12,453,847 | B2 | 10/2025 | Scheffler et al. | |
| 12,476,002 | B2 | 11/2025 | El Katerji et al. | |
| 12,478,266 | B2 | 11/2025 | Edelman et al. | |
| 12,478,267 | B2 | 11/2025 | Schlebusch et al. | |
| 12,478,774 | B2 | 11/2025 | Muller | |
| 12,491,357 | B2 | 12/2025 | Baumbach et al. | |
| 12,494,292 | B2 | 12/2025 | El Katerji et al. | |
| 12,502,524 | B2 | 12/2025 | Stigloher et al. | |
| 12,508,418 | B2 | 12/2025 | Baumbach et al. | |
| 12,521,543 | B2 | 1/2026 | Egler | |
| 12,544,556 | B2 | 2/2026 | Tuval et al. | |
| 12,544,557 | B2 | 2/2026 | Lee et al. | |
| 12,544,559 | B2 | 2/2026 | Barry | |
| 12,569,671 | B2 | 3/2026 | Schellenberg et al. | |
| 12,575,841 | B2 | 3/2026 | Gao et al. | |
| 12,576,261 | B2 | 3/2026 | Vasudevan Jalaja et al. | |
| 12,589,239 | B2 | 3/2026 | Gandhi et al. | |
| 12,611,535 | B2 | 4/2026 | Segura Ortega et al. | |
| 12,629,508 | B2 | 5/2026 | Tuval et al. | |
| 12,629,509 | B2 | 5/2026 | Schwammenthal et al. | |
| 2002/0022785 | A1 | 2/2002 | Romano | |
| 2002/0082585 | A1 | 6/2002 | Carroll et al. | |
| 2002/0093412 | A1 | 7/2002 | Morrison | |
| 2003/0199727 | A1 | 10/2003 | Burke | |
| 2004/0124979 | A1 | 7/2004 | Medema | |
| 2005/0046044 | A1 | 3/2005 | Theuss | |
| 2005/0187487 | A1 | 8/2005 | Azizkhan | |
| 2007/0069354 | A1 | 3/2007 | Dangelmaier | |
| 2008/0248614 | A1 | 10/2008 | Yang | |
| 2008/0287799 | A1 | 11/2008 | Hall | |
| 2009/0212637 | A1 | 8/2009 | Baarman et al. | |
| 2010/0191035 | A1 | 7/2010 | Kang et al. | |
| 2011/0160516 | A1 | 6/2011 | Dague | |
| 2011/0172505 | A1 | 7/2011 | Kim | |
| 2011/0186943 | A1 | 8/2011 | Pahl | |
| 2012/0029408 | A1 | 2/2012 | Beaudin | |
| 2012/0150291 | A1 | 6/2012 | Aber | |
| 2012/0197141 | A1 | 8/2012 | Vanney | |
| 2012/0245404 | A1 | 9/2012 | Smith | |
| 2013/0280692 | A1 | 10/2013 | Gourlay | |
| 2013/0289334 | A1 | 10/2013 | Badstibner | |
| 2013/0304404 | A1 | 11/2013 | Dam | |
| 2014/0030122 | A1 | 1/2014 | Ozaki | |
| 2014/0275727 | A1 | 9/2014 | Bonde | |
| 2015/0027224 | A1 | 1/2015 | Schiffer | |
| 2015/0080743 | A1 | 3/2015 | Siess | |
| 2015/0196076 | A1 | 7/2015 | Billingslea | |
| 2015/0200562 | A1 | 7/2015 | Kilinc et al. | |
| 2015/0201900 | A1 | 7/2015 | Syed | |
| 2016/0151553 | A1 | 6/2016 | Bonde | |
| 2016/0302672 | A1 | 10/2016 | Kuri | |
| 2016/0303299 | A1 | 10/2016 | Muller | |
| 2016/0317043 | A1 | 11/2016 | Campo | |
| 2017/0258981 | A1 | 9/2017 | Franano | |
| 2017/0340789 | A1 | 11/2017 | Bonde et al. | |
| 2017/0347229 | A1 | 11/2017 | Kwon | |
| 2018/0021497 | A1 | 1/2018 | Nunez | |
| 2018/0126053 | A1 | 5/2018 | Zilbershlag et al. | |
| 2018/0333059 | A1 | 11/2018 | Casas | |
| 2020/0028376 | A1 | 1/2020 | Ha | |
| 2021/0298653 | A1 | 9/2021 | Woodard | |
| 2022/0361762 | A1 | 11/2022 | Lalancette | |
| 2025/0032773 | A1 | 1/2025 | Baumbach et al. | |
| 2025/0121177 | A1 | 4/2025 | West | |
| 2025/0143587 | A1 | 5/2025 | Stotz | |
| 2025/0144397 | A1 | 5/2025 | Kassel et al. | |
| 2025/0222247 | A1 | 7/2025 | Schlebusch | |
| 2025/0251330 | A1 | 8/2025 | Stotz | |
| 2025/0281060 | A1 | 9/2025 | Schlebusch et al. | |
| 2025/0319299 | A1 | 10/2025 | Stotz et al. | |
| 2025/0345590 | A1 | 11/2025 | Schlebusch et al. | |
| 2025/0367429 | A1 | 12/2025 | Eggen et al. | |
| 2025/0367431 | A1 | 12/2025 | Baumbach et al. | |
| 2026/0048254 | A1 | 2/2026 | Scheffler et al. | |
| 2026/0060557 | A1 | 3/2026 | Schlebusch et al. | |
| 2026/0083959 | A1 | 3/2026 | Baumbach et al. | |
| 2026/0115450 | A1 | 4/2026 | Stigloher et al. | |

FOREIGN PATENT DOCUMENTS

| | | |
|---|---|---|
| CN | 219250364 | 6/2023 |
| CN | 118320294 | 7/2024 |
| CN | 113769260 | 9/2024 |
| CN | 118920928 | 11/2024 |
| EP | 0 764 448 | 3/1997 |
| EP | 3 378 421 | 9/2018 |
| EP | 3 972 661 | 3/2022 |

(56) References Cited

FOREIGN PATENT DOCUMENTS

| | | |
|---|---|---|
| EP | 4 252 825 | 10/2023 |
| EP | 4 252 826 | 10/2023 |
| EP | 4 252 828 | 10/2023 |
| EP | 3 854 444 | 9/2024 |
| EP | 3 793 674 | 10/2024 |
| EP | 3 618 885 | 11/2024 |
| EP | 4 034 221 | 11/2024 |
| EP | 3 809 960 | 12/2024 |
| EP | 4 477 250 | 12/2024 |
| EP | 4 483 940 | 1/2025 |
| EP | 4 491 213 | 1/2025 |
| EP | 3 854 446 | 2/2025 |
| EP | 4 429 754 | 2/2025 |
| EP | 3 970 785 | 3/2025 |
| EP | 4 429 753 | 3/2025 |
| EP | 3 950 043 | 5/2025 |
| EP | 3 899 964 | 6/2025 |
| EP | 3 948 888 | 6/2025 |
| EP | 3 965 845 | 6/2025 |
| EP | 4 039 319 | 6/2025 |
| EP | 3 668 559 | 8/2025 |
| EP | 3 848 088 | 8/2025 |
| EP | 4 218 556 | 9/2025 |
| EP | 3 911 227 | 1/2026 |
| EP | 4 201 467 | 1/2026 |
| EP | 4 112 115 | 2/2026 |
| EP | 3 492 118 | 4/2026 |
| EP | 4 090 412 | 4/2026 |
| EP | 4 114 504 | 4/2026 |
| EP | 3 852 833 | 5/2026 |
| EP | 4 188 511 | 5/2026 |
| EP | 4 223 356 | 5/2026 |
| EP | 4 252 827 | 5/2026 |
| GB | 2 504 177 | 1/2014 |
| JP | 2010-503495 | 2/2010 |
| JP | 2019-508128 | 3/2019 |
| JP | 2019-509141 | 2/2022 |
| WO | WO 89/006513 | 1/1989 |
| WO | WO 94/009835 | 5/1994 |
| WO | WO 2018/005228 | 1/2018 |
| WO | WO 2018/146045 | 8/2018 |
| WO | WO 2019/158996 | 8/2019 |
| WO | WO 2021/159001 | 8/2021 |
| WO | WO 2023/040546 | 12/2021 |
| WO | WO 2023/226779 | 9/2022 |
| WO | WO 2022183208 | 9/2022 |
| WO | WO 2023/037162 | 3/2023 |
| WO | WO 2023/230157 | 11/2023 |
| WO | WO 2024/104184 | 5/2024 |
| WO | WO 2026/072583 | 4/2026 |

OTHER PUBLICATIONS

"ECG Electrodes product comparison chart," 3M.com, 2018, https://multimedia.3m.com/mws/media/14908830/red-dot-ecg-electrodes-comparison-chart.pdf, accessed May 18, 2025, 1 page.

Eeckhout, MD, PhD, et al., "Handbook of Complications During Percutaneous Cardiovascular Interventions", 2007 Informa UK Ltd., Ch. 12, pp. 167-177.

HeartMate 3™ Left Ventricular Assist System, Instructions for Use, Thoratec Corporation, Aug. 2017, pp. 536. [Uploaded in 3 parts].

Mack-Haynes, Robin, "Fasteners Made Easy," New Mexico State University, https://pubs.nmsu.edu/_c/C232.pdf, accessed May 18, 2025, pp. 8.

Mullins, Charles E., MD, "Cardiac Catheterization in Congenital Heart Disease: Pediatric and Adult", Blackwell Futura, 2006, Chapters 3, 4 and 32, pp. 101.

Sigg et al., "Cardiac Electophysiology Methods and Models", Springer, Clinical Perspective: Electrophysiology in the Young and Patients with Congenital Heart Disease, Ch. 23, 2010, pp. 457-477.

Tan et al., "Surface Engineering and Patterning Using Parylene for Biological Applications." Materials, Mar. 15, 2010, vol. 3, No. 3, pp. 1803-1832.

Radiologyinfo.org, "Subcutaneous Port," Definition, https://www.radiologyinfo.org/en/glossary?id=ezNFREEzNEFFLTI5OTAtNDVFNy04MkVBLTA1RDVGMDdBMzNFRH0=&i=1&b=0&modal=1, accessed Sep. 2, 2025, 1 page.

Walser, Eric, "Venous access ports: indications, implantation technique, follow-up, and complications;" Cardiovasc Intervent Radial, Aug. 2012; vol. 35, No. 4, pp. 751-764. (Abstract Only).

* cited by examiner

METHOD FOR DETERMINING A FLOW RATE OF A FLUID FLOWING THROUGH A CARDIAC ASSIST SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 15/734,353, entitled METHOD FOR DETERMINING A FLOW RATE OF A FLUID FLOWING THROUGH A CARDIAC ASSIST SYSTEM, and filed Jul. 16, 2021, which is the U.S. National Phase of international application number PCT/EP2019/064804, entitled METHOD FOR DETERMINING A FLOW RATE OF A FLUID FLOWING THROUGH AN IMPLANTED VASCULAR SUPPORT SYSTEM, AND IMPLANTABLE VASCULAR SUPPORT SYSTEM, and filed Jun. 6, 2019, which is an International Application of and claims the benefit of priority to German Application No. 102018208929.9, filed Jun. 6, 2018, the disclosure of each of which is hereby incorporated by reference herein in its entirety for all purposes and forms a part of this specification.

BACKGROUND

Field

The invention relates to a method for determining a flow rate of a fluid flowing through an implantable vascular assist system, an implantable vascular assist system, and the use of pulsed Doppler measurements at different pulse repetition rates. The invention is used, in particular, in (fully) implanted left ventricular assist systems (LVAD).

Description of the Related Art

It is known to integrate ultrasonic volume flow sensors in ventricular assist systems in order to find the so-called pump volume flow, which quantifies the fluid volume flow through the assist system itself, with said ultrasonic volume flow sensors. In this case, the ultrasonic volume flow sensors can carry out pulsed Doppler measurements or the pulsed wave Doppler (PWD) method. This method requires only one ultrasonic transducer element and makes it possible to select with a high degree of accuracy the distance of the observation window from the ultrasonic element. In the PWD systems known from the prior art, ultrasonic pulses are emitted at a defined pulse repetition rate (PRF). In this case, the pulse repetition rate must exceed double the maximum occurring Doppler frequency shift in order not to violate the Nyquist theorem. If this condition is not fulfilled, aliasing will occur; that is to say, ambiguities will occur in the detected frequency spectrum.

As a result of the geometric design of the measurement setup in ventricular assist systems (VADs), it may be that the range of measurement or the observation window is so far away from the ultrasonic transducer that the signal transit time of the ultrasonic pulse from the transducer to the range of measurement and back to the transducer cannot be disregarded. Because, in the PWD method, a new ultrasonic pulse may not or rather should not be emitted (at least in theory) until the preceding ultrasonic pulse no long sends any significant echoes, the signal transit time limits the maximum possible pulse repetition rate. At the typically high flow rates, prevailing in ventricular assist systems, and under the geometric boundary conditions for the distance of the observation window from the ultrasonic element, the Nyquist sampling theorem will be inevitably violated, with the result that ambiguities (aliasing) will occur in the spectrum.

Ventricular assist systems with ultrasonic sensors not using the PWD method are usually equipped with two ultrasonic transducers. Although it is possible for the transit time problem described above to occur, this problem can be solved in a different way once these systems are properly implemented. However, ventricular assist systems with ultrasonic sensors using the PWD method are particularly susceptible to the described effect at medium to high flow rates. At the present time, the state of the art requires that the fixed pulse repetition rate be selected in such a way that aliasing does not occur.

SUMMARY

The object of the present invention is to provide an improved method for determining a flow rate of a fluid flowing through an implanted vascular assist system and to provide an improved implanted vascular assist system, in which the flow rate of a fluid flowing through said system can be determined.

In particular, the object of the present invention is to provide a method for determining a flow rate of a fluid and an improved implantable vascular assist system, in which the process of determining the flow rate of a fluid flowing through said system is provided, in which process it is possible to use only one ultrasonic transducer to determine the flow rate at the flow rates prevailing in a ventricular assist system, even in the case of a large signal transit time of an ultrasonic pulse from the ultrasonic transducer to the range of measurement and back.

This object is achieved by means of the method disclosed in and the implantable vascular assist system disclosed herein.

Advantageous embodiments of the invention are disclosed in the dependent claims.

The present invention includes a method for determining a flow rate of a fluid flowing through an implanted vascular assist system, said method comprising the following steps:

a) carrying out a first pulsed Doppler measurement at a first pulse repetition rate by means of an ultrasonic sensor of the assist system,
b) carrying out a second pulsed Doppler measurement at a second pulse repetition rate by means of the ultrasonic sensor of the assist system, wherein the second pulse repetition rate is different from the first pulse repetition rate,
c) determining the flow rate using the measurement results of the first pulsed Doppler measurement and the second pulsed Doppler measurement.

The vascular assist system is preferably a cardiac assist system, particularly preferably a ventricular assist system. The assist system is usually used to help convey the blood in the cardiovascular system of a human being and, if applicable, patients. The assist system can be arranged at least partially in a blood vessel. The blood vessel is, for example, the aorta, in particular in the case of a left ventricular assist system; or the blood vessel is the common trunk (Truncus pulmonalis) that is divided into the two pulmonary arteries, in particular in the case of a right ventricular assist system. The assist system is preferably arranged at the outlet of the left ventricle of the heart or the left chamber of the heart. It is particularly preferable for the assist system to be arranged in the position of the aortic valve.

The solution proposed herein helps, in particular, to compensate for the aliasing effects in a medical pulsed wave Doppler system. The method can help to determine the fluid flow rate and/or a fluid volume flow from a ventricle of a heart, in particular from a (left) ventricle of a heart to the aorta in the region of a (fully) implanted (left) ventricular assist system. As a rule, the fluid is blood. The flow rate is determined in a fluid flow or the fluid volume flow that flows through the assist system, in particular through a (inlet) cannula of the assist system. The method allows the flow rate and/or the fluid volume flow of the blood flow to be determined in an advantageous way with high quality even outside the surgery scenario, in particular by means of the implanted assist system itself.

In the solution proposed here, a correlation between the measured (main) peak in the Doppler frequency spectrum and the applied pulse repetition rate (PRF) can be used in a particularly advantageous manner. If a measurement is carried out several times at different PRFs, then the best possible maxima of the respective measurement cycle with modified PRF are located at a different position in the frequency spectrum. As a result, a system of equations can be set up in an advantageous way by varying the PRF values, and said system of equations can be used to eliminate the ambiguities and to find unique solutions. This aspect makes it possible to calculate in a particularly advantageous manner the main rate component of a blood flow despite a so-called "spectrum wrapping" or despite aliasing.

In step a), a first pulsed Doppler measurement is carried out at a first pulse repetition rate (first PRF or $PRF_1$) by means of an ultrasonic sensor of the assist system. In particular, the pulsed wave Doppler (PWD) method is used to carry out the pulsed Doppler measurement. In particular, a first PWD measurement cycle is run in step a).

In step b), a second pulsed Doppler measurement is carried out at a second pulse repetition rate (second PRF or $PRF_2$) by means of the ultrasonic sensor of the assist system. In this case, the second pulse repetition rate differs from the first pulse repetition rate. For example, the second pulse repetition rate is greater than or less than the first pulse repetition rate. In other words, this means in particular that the first pulse repetition rate and the second pulse repetition rate are pulse repetition rates that are different from one another. In particular, a second PWD measurement cycle is run in step b). In addition, a repetition of a PWD measurement cycle with different fixed PRF values, for example, 20 kHz and 25 kHz, is preferably carried out in steps a) and b).

Other (pulsed) Doppler measurements, for example a third, fourth, and/or fifth Doppler measurement, can also be carried out. For these measurements, the situations listed in conjunction with the first and second pulsed Doppler measurement may apply correspondingly. In particular, all of these pulsed Doppler measurements have pulse repetition rates that are different from one another. If other Doppler measurements are carried out, they can be included (as needed) in the determination process in step c). In other words, this means in particular that the process of determining the flow rate can also be carried out using the measurement results of the first pulsed Doppler measurement, the second pulsed Doppler measurement, and other pulsed Doppler measurements (insofar as they are available). However, the number of Doppler measurements is preferably just large enough that a unique flow rate can be determined by means of the method, an aspect that can be achieved here in a particularly advantageous manner with two Doppler measurements.

A PWD measurement cycle comprises, in particular, a sequence of a (defined) number of successively emitted ultrasonic pulses. The Doppler measurements that are carried out at different PRFs in steps a) and b) are basically carried out with respect to the same fluid flow, for example in the same observation window or in the same range of measurement. In other words, this means in particular that the first pulsed Doppler measurement and the second pulsed Doppler measurement take place within the same observation window or range of measurement. In addition, it is advantageous for the two pulsed Doppler measurements to follow one another immediately in terms of time or for there to be no significant time interval between the two measurements.

In step c), the flow rate is determined using the measurement results of the first pulsed Doppler measurement and the second pulsed Doppler measurement. As a rule, the measurement results are ambiguous. This ambiguity can be explained, in particular, by the fact that there is generally a violation of the Nyquist sampling theorem here. This violation of the Nyquist sampling theorem is caused, in particular, by the fact that there are comparatively long signal transit times between the ultrasonic sensor and the observation window or the range of measurement in the assist system and, in the case of the pulsed Doppler measurements, a new ultrasonic pulse is usually not emitted until an echo of a just previously emitted ultrasonic pulse has been received.

The flow rate can be determined, for example, in such a way that initially a first Doppler frequency spectrum is detected on the basis of the first pulsed Doppler measurement and a second Doppler frequency spectrum is detected on the basis of the second pulsed Doppler measurement. In other words, this means in particular that, initially, a calculation of the (respective) Doppler frequency spectrum is carried out for each PRF measurement. For example, a first main frequency component of the first Doppler frequency spectrum and a second main frequency component of the second Doppler frequency spectrum can also be determined. In other words, this means in particular that a determination of the main frequency component of the (respective) Doppler spectrum (for example, single frequency peak or a so-called "template matching" of the expected frequency distribution) takes place.

A system of equations can be set up by way of example on the basis of the first main frequency component and the second main frequency component. The system of equations can be solved, for example, by setting and solving the resulting linear Diophantine equation (for example, solvable by Bezout coefficients). The actual or unique Doppler frequency can be determined from this solution. This (unique) Doppler frequency can be used to calculate the flow rate in the usual manner.

In accordance with one advantageous embodiment, it is proposed that at least in one of the two steps a) and b), a new ultrasonic pulse is emitted only after an echo of a just previously emitted ultrasonic pulse has been received. In both steps a) and b), a new ultrasonic pulse is emitted preferably only after an echo of a just previously emitted ultrasonic pulse has been received. Preferably, a new ultrasonic pulse is not emitted until all (significant) echoes of a just previously emitted ultrasonic pulse have been received.

In accordance with one advantageous embodiment, it is proposed that a maximum pulse repetition rate of the pulsed Doppler measurements may be smaller and/or smaller than twice a maximum occurring Doppler shift. The maximum pulse repetition rate of the pulsed Doppler measurements is preferably smaller than the maximum occurring or the expected Doppler shift. If the maximum pulse repetition rate is less than twice the maximum occurring Doppler shift, then, in principle, the Nyquist sampling theorem will inevitably be violated. However, this violation may be necessary in order to be able to carry out a PWD method in a vascular assist system.

In accordance with one advantageous embodiment, it is proposed that a correlation between a detected main frequency component of the Doppler frequency spectrum (in particular, peak in the Doppler contribution to the frequency spectrum) of a pulsed Doppler measurement and the pulse repetition rate applied for this Doppler measurement be used in step c). The main frequency component of the (respective) Doppler frequency spectrum is basically the frequency component that is characteristic of the measured flow rate. The main frequency component is, in particular, a (local) maximum, a (local) amplitude, or a (secondary) peak in the Doppler frequency spectrum ("in the Doppler frequency spectrum" is here, in particular, a short form for "in the Doppler contribution to the frequency spectrum"; this is meant to clarify that the peak does not mean the (ever larger) carrier line in the spectrum). A correlation between a detected peak in the Doppler frequency spectrum of a pulsed Doppler measurement and the pulse repetition rate applied for this Doppler measurement is preferably used in step c). Furthermore, the first and the second pulsed Doppler measurement cycle are preferably used or set up in each case for this correlation.

In accordance with one advantageous embodiment, it is proposed that a linear equation system be solved in step c), where a Doppler shift is shown as a function of main frequency components of the first pulsed Doppler measurement and the second pulsed Doppler measurement. The Doppler shift can also be referred to as a Doppler frequency (formula symbol df or Δf). In the linear equation system, the Doppler shift is used preferably as a function of the main frequency components and the (different) pulse repetition rates of the first pulsed Doppler measurement and the second pulsed Doppler measurement. The number of equations in the equation system generally corresponds to the number of Doppler measurements that have been carried out. The linear equation system preferably comprises, in particular, two linear equations. In this case, the first linear equation preferably gives the Doppler shift as a function of the main frequency component of the first Doppler frequency spectrum and/or the first pulse repetition rate. The second linear equation preferably gives the Doppler shift as a function of the main frequency component of the second Doppler frequency spectrum and/or the second pulse repetition rate.

In accordance with an additional advantageous embodiment, it is proposed that a linear Diophantine equation be set up on the basis of the linear equation system. A linear Diophantine equation is an equation of the form $a_1x_1+a_2x_2+a_3x_3+\ldots+a_nx_n+c=0$ with integer coefficients ai, where, in this case in particular the solutions of interest are the integer ones. Linear means that the variables $x_i$ do not occur in powers greater than one. The linear Diophantine equation can be set up, for example, in such a way that the two linear equations are resolved after the Doppler shift and are subsequently equated.

In accordance with another advantageous embodiment, it is proposed that the linear Diophantine equation be solved using Bezout coefficients or a method of exhaustion. The so-called Bezout coefficients can be determined, in particular, by solving the equation $n_1 \cdot PRF_1+n_2 \cdot PRF_2=ggT(PRF_1, PRF_2)$. Said equation shows, in particular, that the largest common divisor ggT of two integer numbers, for example PRF1 and PRF2, can be shown as a linear combination of the integer coefficients $n_1$ and $n_2$. The Bezout coefficients determined in this way are used, in particular, to solve the Diophantine equation that has been set up. The method of exhaustion can also be referred to as a so-called "brute force" method. This method describes a solution method that is based on trying all possible (or at least many possible) cases.

In accordance with one advantageous embodiment, it is proposed that the flow rate be used to determine a fluid volume flow through the assist system. In other words, said fluid volume flow relates in particular to the fluid volume flow of a fluid that flows (only) through the assist system itself, for example through an (inlet) cannula of the assist system. This fluid volume flow is usually the so-called pump volume flow ($Q_p$), which quantifies only the flow through the assist system itself. If this value is known in addition to the total volume flow or the heart-time volume ($Q_{HTV}$), then the so-called assist level can be calculated from the ratio of $Q_p$ to $Q_{HTV}$ (i.e., $Q_P/Q_{HTV}$). In order to determine the fluid volume flow, the determined flow rate can be multiplied, for example by a cross section of the assist system through which cross section the fluid can flow, in particular a cross section of a cannula through which cross section the fluid can flow.

In accordance with a further aspect, an implantable vascular assist system is proposed, comprising:

- an ultrasonic sensor designed to carry out pulsed Doppler measurements at different pulse repetition rates,
- a processing unit designed to determine a flow rate of a fluid flowing through the assist system, using the measurement results of the pulsed Doppler measurements at different pulse repetition rates.

The assist system is preferably a left ventricular assist system (LVAD) or a percutaneous, minimally invasive left heart assist system. Furthermore, it is preferably fully implantable. In other words, this means in particular that the means required for detection, in particular the ultrasonic sensor, are located completely in the body of the patient and remain there. The assist system can also be constructed of multiple parts or a plurality of components that can be arranged at a distance from one another, so that, for example, the ultrasonic sensor and the processing unit (measurement unit) can be arranged so as to be separated from one another by means of a cable. In the multipart embodiment, the processing unit, which is arranged separately from the ultrasonic sensor, can also be implanted or even arranged outside the body of the patient. In any case, it is not absolutely necessary for the processing unit to also be arranged in the body of the patient. For example, the assist system can be implanted in such a way that the processing unit is arranged on the skin of the patient or outside the body of the patient and a connection to the ultrasonic sensor arranged in the body is established. The assist system is particularly preferably designed or lends itself in such a way that it can be arranged at least partially in one ventricle, preferably the left ventricle of a heart and/or an aorta, in particular in the aortic valve position.

Furthermore, the assist system preferably comprises a cannula, in particular an inlet cannula, a continuous flow machine, for example a pump, and/or an electric motor. In this case, the electric motor is usually a component of the continuous flow machine. The (inlet) cannula is preferably designed in such a way that in the implanted state it can guide fluid out of a (left) ventricle of a heart to the continuous flow machine. The assist system preferably is formed in an elongated and/or tubular manner. The cannula and the continuous flow machine are arranged in the region of the opposite ends of the assist system.

In particular, exactly and only one ultrasonic sensor is provided. The ultrasonic sensor has preferably exactly and only one ultrasonic transducer element. This is sufficient for a Doppler measurement, especially if the PWD method is used.

The assist system is advantageously designed to carry out a method proposed herein.

In accordance with another aspect, it is proposed that pulsed Doppler measurements at different pulse repetition rates be used to correct an ambiguous measurement result of an ultrasonic sensor of an implanted vascular assist system. Preferably, at least one method proposed herein or an assist system proposed herein is used to correct an ambiguous measurement result of the ultrasonic sensor.

The details, features, and advantageous embodiments explained in conjunction with the method can also appear correspondingly in the assist system presented herein and/or in the use thereof and vice versa. To this extent, reference is made in full to said explanations in order to characterize the features in more precise detail.

BRIEF DESCRIPTION OF THE DRAWINGS

The solution presented herein and the technical environment thereof are explained in greater detail below with reference to the figures. It should be noted that the invention is not to be limited by the exemplary embodiments shown. In particular, unless explicitly stated otherwise, it is also possible to extract partial aspects of the situation explained in the figures and to combine them with other components and/or findings from other figures and/or the present description. The drawings show the following in schematic form.

DETAILED DESCRIPTION

Figure 1:
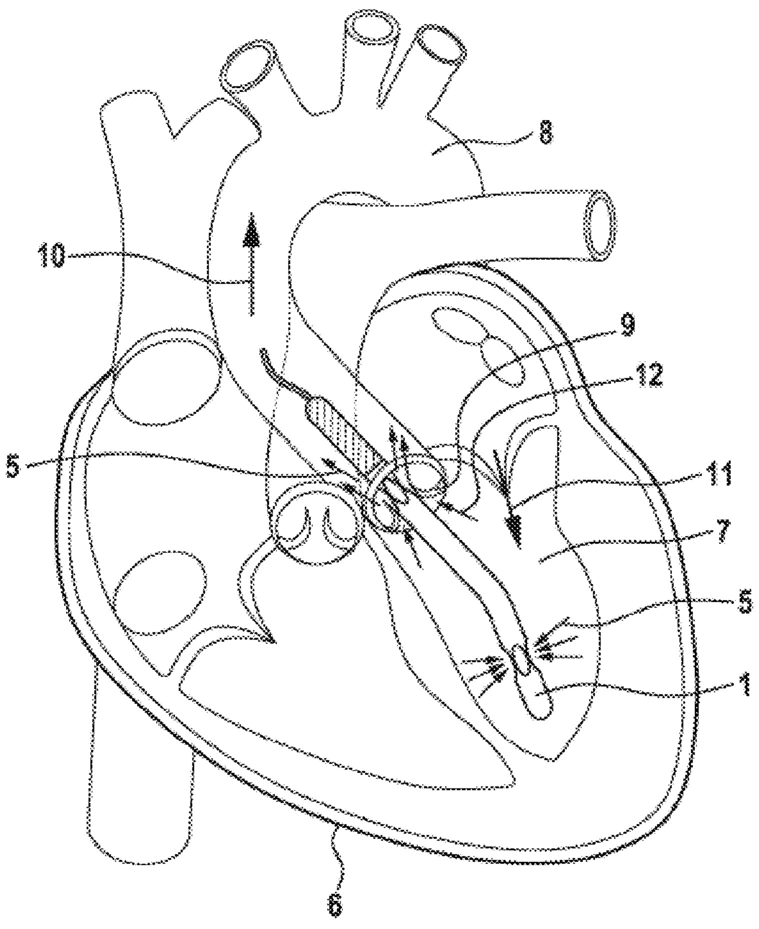
FIG. 1 an implanted vascular assist system in a heart.

FIG. 1 shows in schematic form an implanted vascular (here: ventricular) assist system 1 in a heart 6. The assist system 1 assists the heart 6 by helping to convey blood out of the (left) ventricle 7 into the aorta 8. For this purpose, the assist system 1 is anchored in the aortic valve 9, as illustrated by way of example in FIG. 1. At a level of assist of 100%, the assist system 1 (LVAD) conveys the complete blood volume flow. The level of assist describes the proportion of the volume flow conveyed through a delivery means such as a pump of the assist system 1 or through the assist system 1 to the total volume flow of blood from the ventricle 7 to the aorta 8.

Therefore, at an assist level of 100%, the total fluid volume flow 10 from the ventricle 7, the volume flow 11 from the heart valve into the ventricle 7, and the fluid volume flow 5 through the assist system 1 are identical. In this case, it follows that the aortic valve volume flow or bypass volume flow 12 (formula symbol: $Q_a$) is zero. The total fluid volume flow 10 can also be described as the (total) heart-time volume (HTV, formula symbol: $Q_{HTV}$). The fluid volume flow 5 can also be referred to as a so-called pump volume flow (formula symbol: $Q_p$), which quantifies only the flow through the assist system 1 itself. As a result, the level of assist can be calculated from the ratio $Q_P/Q_{HTV}$.

In the case of lower levels of assist and healthier hearts with a strong ventricular contraction, the heart 6 continues to fulfill its function to a certain extent, so that during systole (heart muscle contracts and pushes the blood out into the aorta 8 as a result of the decrease in volume of the ventricle 7), a pulsatile volume flow component 12 (bypass) is produced by the heart valve or the aortic valve 9. At the same time, the pressure difference in the assist system 1, in particular in the pump typically provided (not shown here) in the assist system 1, drops, so that correspondingly the assist system 1 also conveys an increased amount of fluid volume flow 5 during systole.

Figure 2:
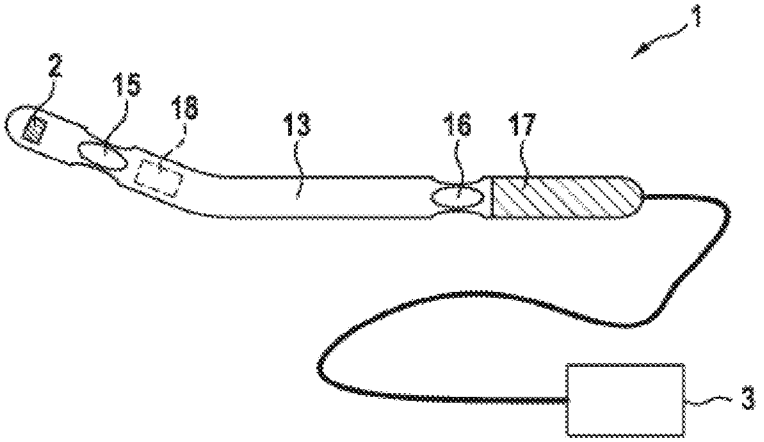
FIG. 2 the assist system from FIG. 1.

FIG. 2 shows in schematic form the assist system 1 from FIG. 1. The assist system 1 comprises an ultrasonic sensor 2, which is designed to carry out pulsed Doppler measurements at different pulse repetition rates, and a processing unit 3 that is designed to determine a flow rate of a fluid (here: blood) flowing through the assist system 1, using the measurement results of the pulsed Doppler measurements at different pulse repetition rates.

In addition, FIG. 2 also shows by way of example that the ultrasonic sensor 2 can be integrated in the tip of a cannula 13 of the assist system 1. The ultrasonic sensor 2 helps to determine the flow rate (amount and at least one direction) of a fluid or fluid volume flow 5, which flows through the assist system 1 and which is also referred to as a pump volume flow ($Q_p$). For this purpose, the ultrasonic sensor 2 is designed to carry out pulsed Doppler measurements in the fluid inside the cannula 13. The fluid can enter the interior of the cannula 13 through one or more inlet openings 15 (from the ventricle 7) and exit through one or more outlet openings 16 (into the aorta 8). In order to assist the fluid flow through the assist system 1, in particular through the cannula 13, the assist system 1 includes here a continuous flow machine 17. The continuous flow machine 17 is generally formed in the manner of a pump. Furthermore, an observation window or a range of measurement 18 of the ultrasonic sensor 2 is also shown by way of example in FIG. 2.

Figure 3:
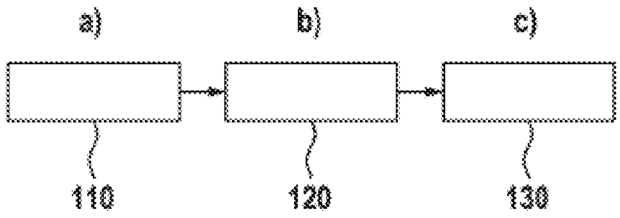
FIG. 3 a sequence of a method presented here in a normal operating mode.

FIG. 3 shows in schematic form a sequence of a method presented here in a normal operating mode. The method is used to determine a flow rate of a fluid flowing through an implanted vascular assist system 1 (see FIGS. 1, 2). The illustrated sequence of process steps a), b), and c) with the blocks 110, 120, and 130 is shown merely for illustrative purposes. In block 110, a first pulsed Doppler measurement is carried out at a first pulse repetition rate by means of an ultrasonic sensor 2 of the assist system 1. In block 120, a second pulsed Doppler measurement is carried out at a second pulse repetition rate by means of the ultrasonic sensor 2 of the assist system 1, where, in this case, the second pulse repetition rate differs from the first pulse repetition rate. In block 130, the flow rate is determined using the measurement results of the first pulsed Doppler measurement and the second pulsed Doppler measurement.

The following parameters are assumed for an exemplary representation of the method:

- diameter inlet region or range of measurement, e.g. 5 mm,
- maximum blood flow to be measured, e.g. Q=9 l/min.,
- resulting maximum blood flow rate: $v_{blood,max}$=7.64 m/s,
- speed of sound in the blood, e.g. $c_{blood}$=1,540 m/s,
- ultrasonic frequency, e.g. $f_0$=6 MHz,
- distance of the ultrasonic element from the start of the observation window, e.g. 25 mm, number of ultrasonic vibration cycles per emitted ultrasonic PWD pulse, e.g. 10, resulting burst length (in distance): $l_{burst}=c_0\times 10/f_0=2.57$ mm, resulting maximum propagation distance ultrasonic burst: d=55.13 mm.

The above data gives the following (expected) maximum Doppler shift for a measurement directly in the emission direction (flow direction corresponds to the main emission direction; α=0):

$$df = \frac{2\cdot v_{blood,max}\cdot f_0}{c_0} = \frac{2\cdot 7.64\frac{m}{s}\cdot 6\text{ MHz}}{1540\frac{m}{s}} = 59.53\text{ kHz} \tag{1}$$

The measurement should be carried out as a pulsed Doppler measurement, in which a new ultrasonic pulse is not emitted until an echo of a just previously emitted ultrasonic pulse has decayed. The choice of the pulse repetition rate (PRF) to be used for this purpose is explained below.

Taking into account the (Nyquist) sampling theorem (which, however, does not have to be and is not taken into account in the solution presented here), a maximum Doppler frequency of 59.53 kHz would mean that a minimum pulse repetition rate or a minimum pulse repetition frequency of $$PRF_{min} = 2\cdot df = 119.06\text{ kHz} \tag{2}$$

would have to be observed.

However, in the implanted vascular assist systems that are the focus of the present invention, the following maximum pulse repetition rate PRF-$_{max}$—is calculated from the geometric consideration (maximum propagation distance of the ultrasonic pulse) or the geometric boundary conditions in the assist system and the resulting transit time of all of the relevant signal components:

$$PRF_{max} = \frac{c_{blood}}{d} = 27.93\text{ kHz} \tag{3}$$

Therefore, the maximum pulse repetition rate of the pulsed Doppler measurements here (i.e. for the assist systems that are the focus of the present invention) is smaller than twice the maximum occurring Doppler shift.

These boundary conditions lead to a violation of the sampling theorem and, consequently, to an ambiguity of the measurement results that can be corrected by an evaluation, as described in the following sections.

Figure 4:
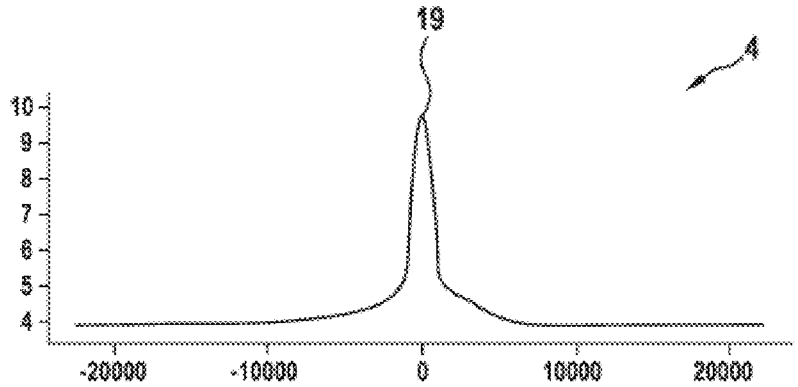
FIG. 4 an exemplary Doppler frequency spectrum.
Figure 5:
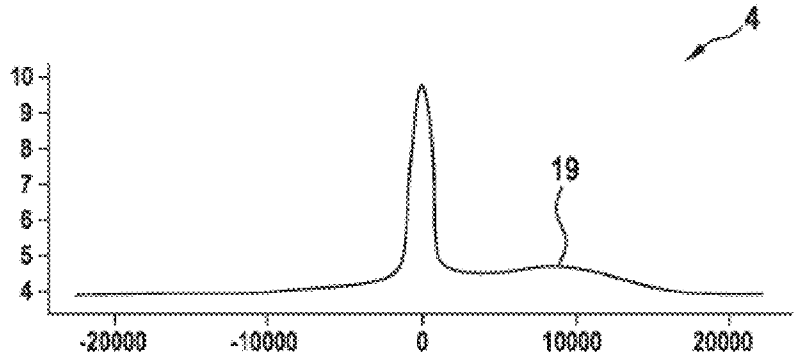
FIG. 5 another exemplary Doppler frequency spectrum.

However, in order to illustrate the problems arising from these boundary conditions, the ambiguity occurring in this case is illustrated in FIGS. 4 and 5 (said ambiguity can be resolved with the solution presented here). FIG. 4 shows in schematic form an exemplary Doppler frequency spectrum 4. FIG. 4 shows a Doppler shift at a pulse repetition rate of approximately 25 kHz. The main frequency component 19 (peak) is below the carrier frequency at approximately 0 Hz. FIG. 5 shows in schematic form another exemplary Doppler shift frequency spectrum 4. FIG. 5 shows a Doppler shift at a pulse repetition rate of approximately 20 kHz. The main frequency component 19 (peak) is at approximately +8 kHz.

In the following sections, an exemplary evaluation of the ambiguous measurement results is described in the context of the solution proposed herein.

Two measurement cycles (sequence of a defined number of ultrasonic pulses emitted in succession) at different PRFs (with respect to the same fluid flow, for example in the same observation window) are included. The actual Doppler shift can be shown as a function of the resulting heart frequency components 19, here peaks $f_1$ and $f_2$:

$$df = f_1 + n_1\cdot PRF_1 \tag{4}$$

$$df = f_2 + n_2\cdot PRF_2 \tag{5}$$

This illustrates by way of example how a linear equation system can be set up, in which the Doppler shift df is shown as a function of main frequency components 19, here peaks $f_1$ and $f_2$, of the first pulsed Doppler measurement and the second pulsed Doppler measurement. In addition, this illustrates by way of example a correlation between a detected main frequency component 19 of the Doppler frequency spectrum, here a peak in the Doppler frequency spectrum, a pulsed Doppler measurement, and the pulse repetition rate applied for this Doppler measurement.

By resolving both equations after the Doppler shift df and subsequently equating, the following Diophantine equation is obtained:

$$n_1\cdot PRF_1 - n_2\cdot PRF_2 = f_2 - f_1 \tag{6}$$

This illustrates by way of example how a linear Diophantine equation can be set up on the basis of the linear equation system.

At the speed of sound in blood $c_{blood}$, the ultrasonic transmission frequency $f_0$, the flow rate of the blood $v_{blood}$, and an integer pulse repetition rate, an unambiguous solution can be found for this equation.

$$-|a| \le n_1 \le |a| \text{ where } a = \frac{PRF_2}{2\cdot ggT(PRF_1, PRF_2)} \tag{7}$$

$$-|b| \le n_2 \le |b| \text{ where } b = \frac{PRF_1}{2\cdot ggT(PRF_1, PRF_2)} \tag{8}$$

$$v < \frac{a\cdot PRF_1\cdot c_0}{2\cdot f_0} \text{ where } PRF_1 < PRF_2 \tag{9}$$

In this case, the operator ggT represents the largest common divisor. Within these ranges, this equation can be obtained, for example, with the aid of Bezout coefficients or with an exhaustion (brute force) approach.

This procedure is illustrated by way of example with the aid of the values v=8 m/s, $f_0$=4 MHz, $PRF_1$=11 kHz and $PRF_2$=19 kHz. At these values, the resulting peaks were detected at $f_1$=−2442 Hz and $f_2$=3558 Hz. The resulting Diophantine equation is:

$$n_1\cdot 11 - n_2\cdot 19 = 6 \tag{10}$$

The largest common divisor for this case is 1, and the Bezout coefficients are 7 and 4. This gives the following possible solutions:

$$n_1 = 6 \cdot 7 + m \cdot 19 = 4 + m \cdot 19 \quad (11)$$

$$n_2 = 6 \cdot 4 + m \cdot 11 = 2 + m \cdot 11 \quad (12)$$

This illustrates by way of example how the linear Diophantine equation can be solved using Bezout coefficients.

Because a unique solution can be determined only for m=0, only this is considered. It can be used to determine the frequency of the Doppler shift that is now no longer ambiguous. Both equations give the same result.

$$\begin{aligned} df &= f_1 + n_1 \cdot PRF_1 & (13) \\ &= -2442\ \text{Hz} + 4 \cdot 11000\ \text{Hz} = 41558\ \text{Hz} & (14) \\ df &= f_2 + n_2 \cdot PRF_2 & (15) \\ &= -3558\ \text{Hz} + 2 \cdot 19000\ \text{Hz} = 41558\ \text{Hz} & (16) \end{aligned}$$

The flow rate of the fluid flowing through the assist system 1 (here: blood) can be calculated on this basis by means of the frequency shift due to the Doppler effect:

$$df = f_0 \cdot \frac{2v}{c} \cdot \cos(\alpha) \quad (17)$$

where df is the resulting (unique) Doppler frequency shift; $f_0$ the frequency of the emitted ultrasonic pulse; v the flow rate of the medium (sought here); c the speed of sound in the medium; and a the angle between the ultrasonic sound path and the main flow direction.

In a (ventricular) assist system, v is sought, and α, $f_0$ and c are generally known (at least approximately). It is possible to compensate for the ambiguity usually occurring in such (ventricular) assist systems as discussed above in a particularly advantageous way by means of the solution proposed herein. On the basis of the determined flow rate, the fluid volume flow through the assist system can be determined using the (known) geometric boundary conditions in the assist system (known cross section of the range of measurement or the observation region through which the fluid can flow). Said fluid volume flow can help, at least approximately, to detect the blood volume that is actually conveyed through a (heart) assist system. This knowledge of the volume of blood that is actually pumped by a ventricular assist system or a cardiac assist system is medically of great importance, in particular for controlling the (implanted) assist system.

The solution presented herein makes possible one or more of the following advantages, in particular:

Pulsed Doppler measurement or PWD-based flow rate measurement or volume flow measurement is also made possible even with a large distance between the measurement window and the ultrasonic transducer.

Resolution of the geometrically induced ambiguity of the Doppler shift on the basis of geometric boundary conditions in the assist system.

The invention claimed is:

1. A method for determining a flow rate of blood flowing through a cardiac assist system, comprising:

performing a first pulsed Doppler measurement at a first pulse repetition rate using an ultrasonic sensor of the cardiac assist system;

performing a second pulsed Doppler measurement at a second pulse repetition rate using the ultrasonic sensor of the cardiac assist system, wherein the second pulse repetition rate differs from the first pulse repetition rate; and determining the flow rate using measurement results of the first pulsed Doppler measurement and the second pulsed Doppler measurement using a linear Diophantine equation.

2. The method of claim 1, wherein at least one of performing the first pulsed doppler measurement and performing the second pulsed doppler measurement comprises emitting a new ultrasonic pulse using an ultrasonic element only after an echo of an immediately previously emitted ultrasonic pulse has been received by the ultrasonic sensor.

3. The method of claim 1, wherein the first pulse repetition rate or the second pulse repetition rate is smaller than twice a maximum occurring Doppler shift.

4. The method of claim 1, wherein determining the flow rate comprises using a correlation between a detected main frequency component of a Doppler frequency spectrum of the first pulsed Doppler measurement and the first pulse repetition rate or the second pulsed Doppler measurement and the second pulse repetition rate.

5. The method of claim 1, wherein determining the flow rate comprises solving the linear Diophantine equation using Bezout coefficients or an exhaustion method.

6. The method of claim 1, wherein an observation window of the ultrasonic sensor is in a range of 25 mm to 55 mm from an ultrasonic element of the ultrasonic sensor.

7. The method of claim 1, wherein the ultrasonic sensor is configured to perform the first pulsed Doppler measurement and the second pulsed Doppler measurement within a cannula of the cardiac assist system.

8. The method of claim 7, wherein the ultrasonic sensor is integrated into a tip of the cannula.

9. The method of claim 1, wherein an observation window of the ultrasonic sensor is positioned downstream of the ultrasonic sensor.

10. The method of claim 1, wherein the ultrasonic sensor is positioned upstream of a flow machine of the cardiac assist system.

11. The method of claim 1, further comprising determining a fluid flow based on the flow rate.

12. A cardiac assist system comprising:

an ultrasonic sensor configured to perform a first pulsed Doppler measurement at a first pulse repetition rate and a second pulsed Doppler measurement at a second pulse repetition rate, wherein the second pulse repetition rate differs from the first pulse repetition rate; and a processing unit configured to:

determine a flow rate of a fluid flowing through the cardiac assist system using measurement results of the first pulsed Doppler measurement and the second pulsed Doppler measurement, wherein determining the flow rate using the measurement results of the first pulsed Doppler measurement and the second pulsed Doppler measurement comprises using a linear Diophantine equation.

13. The cardiac assist system of claim 12, wherein the processing unit is configured to solve the linear Diophantine equation using Bezout coefficients or an exhaustion method to determine the flow rate.

14. The cardiac assist system of claim 12, wherein the processing unit is configured to calculate a fluid flow based on the flow rate.

15. The cardiac assist system of claim 12, wherein the ultrasonic sensor comprises an observation window in a range of 25 mm to 55 mm from an ultrasonic element of the ultrasonic sensor.

16. The cardiac assist system of claim 12, further comprising a cannula, wherein the ultrasonic sensor is configured to perform the first pulsed Doppler measurement and the second pulsed Doppler measurement within the cannula.

17. The cardiac assist system of claim 16, wherein the ultrasonic sensor is integrated into a tip of the cannula.

18. The cardiac assist system of claim 12, wherein an observation window of the ultrasonic sensor is positioned downstream of the ultrasonic sensor.

19. The cardiac assist system of claim 12, wherein the ultrasonic sensor is positioned upstream of a flow machine of the cardiac assist system.

* * * * *